(12) United States Patent
Nowicki et al.

(10) Patent No.: US 10,295,410 B2
(45) Date of Patent: May 21, 2019

(54) SYSTEMS AND METHODS FOR THE REMOTE DETECTION OF GREENHOUSE ATMOSPHERIC GAS

(71) Applicant: Quantum Spatial, Inc., St. Petersburg, FL (US)

(72) Inventors: Scott Nowicki, Albuquerque, NM (US); Keith Nowicki, Nederland, CO (US)

(73) Assignee: Quantum Spatial, Inc., St. Petersburg, FL (US)

( * ) Notice: Subject to any disclaimer, the term of this patent is extended or adjusted under 35 U.S.C. 154(b) by 0 days.

(21) Appl. No.: 15/694,714

(22) Filed: Sep. 1, 2017

(65) Prior Publication Data

US 2018/0180483 A1 Jun. 28, 2018

Related U.S. Application Data

(60) Provisional application No. 62/437,942, filed on Dec. 22, 2016, provisional application No. 62/437,956, filed on Dec. 22, 2016.

(51) Int. Cl.

| | |
|---|---|
| *G01J 5/00* | (2006.01) |
| *G02B 17/08* | (2006.01) |
| *G01J 5/08* | (2006.01) |
| *G02B 27/42* | (2006.01) |

(52) U.S. Cl.
CPC ............. *G01J 5/0014* (2013.01); *G01J 5/007* (2013.01); *G01J 5/0806* (2013.01); *G02B 17/0848* (2013.01); *G02B 17/0852* (2013.01); *G02B 17/0876* (2013.01); *G02B 27/4205* (2013.01)

(58) Field of Classification Search
CPC ........ G01J 5/0014; G01J 5/007; G01J 5/0806; G02B 17/0848; G02B 17/0852; G02B 27/4205
See application file for complete search history.

(56) References Cited

U.S. PATENT DOCUMENTS

| | | | |
|---|---|---|---|
| 2010/0301214 A1* | 12/2010 | Jonsson | G01N 21/3518 250/332 |
| 2013/0050466 A1* | 2/2013 | Cetin | G01J 3/36 348/82 |
| 2013/0327942 A1* | 12/2013 | Silny | G01N 21/3504 250/339.02 |

(Continued)

*Primary Examiner* — Christine S. Kim
(74) *Attorney, Agent, or Firm* — Fisherbroyles, LLP

(57) ABSTRACT

Disclosed systems and methods for the remote detection of atmospheric gas may include (1) receiving, at a collector, thermal infrared energy from at least one atmospheric column, (2) receiving, at optical subsystems, the thermal infrared energy over optical paths, (3) focusing the thermal infrared energy onto diffraction gratings that disperse the thermal infrared energy at a wavelength within a mid-wavelength infrared (MWIR) spectral region and a wavelength within a long-wavelength infrared (LWIR) spectral region, (4) receiving, at detectors, the thermal infrared energy dispersed from the diffraction gratings within the MWIR spectral region and the LWIR spectral region, (5) determining spectral component data associated with the thermal infrared energy in the MWIR spectral region and the LWIR spectral region, (6) sending the spectral component data to a computing device, and (7) identifying an atmospheric gas based on the spectral component data.

13 Claims, 4 Drawing Sheets

(56) References Cited

U.S. PATENT DOCUMENTS

2014/0002667 A1* 1/2014 Cheben .............. G01N 21/3518
348/164
2015/0371386 A1* 12/2015 Zeng .................... G06T 7/0026
382/171

* cited by examiner

SYSTEMS AND METHODS FOR THE REMOTE DETECTION OF GREENHOUSE ATMOSPHERIC GAS

CROSS-REFERENCE TO RELATED APPLICATIONS

This patent application claims priority to U.S. Patent Application Ser. No. 62/437,942, filed Dec. 22, 2016 and entitled "Systems for the Remote Detection of Atmospheric Gas" and to U.S. Patent Application Ser. No. 62/437,956, filed Dec. 22, 2016 and entitled "Method for the Remote Detection of Atmospheric Gas," of which the disclosures are incorporated herein, in their entirety, by reference.

TECHNICAL FIELD

Embodiments of the disclosure relate generally to atmospheric gas detection, and more specifically, to the use of thermal spectroscopic analysis across multiple wavelengths to detect the presence of greenhouse atmospheric gas.

BACKGROUND

Methane is emitted from natural and anthropogenic sources including fossil fuel extraction and processing, farming, permafrost thawing, ocean-floor methane-hydrate mobilization, landfills and infrastructure leaks and failure. Professional ground and/or aerial inspections may include detecting natural gas transmission and distribution lines for leaks and failures, monitoring gas facilities or wellfields for leaks, and mapping the presence of naturally occurring seeps and plumes for harmful concentrations of greenhouse gases such as methane. Thus, the ability to detect the occurrence of methane leaks and natural sources, map their distribution, and quantify emission rates at high spatial resolution over wide areas can be incredibly useful for a number of industries and applications from energy exploration to environmental monitoring. Current remote methods for detecting methane, which include utilizing spectral analysis techniques, have a number of drawbacks including requiring robust atmospheric corrections and scene-dependent analytics in order to quantitatively map the presence and concentration of methane. It is with respect to these considerations and others that the various embodiments of the present invention have been made.

SUMMARY

As will be described in greater detail below, the disclosure describes various systems and methods for the remote detection of greenhouse atmospheric gas.

In one example, a system for the remote detection of greenhouse atmospheric gas may include a collector that receives thermal infrared energy from a column of atmosphere, and multiple optical subsystems including focusing elements and diffraction gratings in optical alignment with the collector. The optical subsystems may be operative to receive the incoming thermal infrared energy at the collector and focus, with the focusing elements, the thermal infrared energy onto the diffraction gratings. The diffraction gratings may disperse the thermal infrared energy at a wavelength within a mid-wavelength infrared (MWIR) spectral region and a wavelength within a long-wavelength infrared (LWIR) spectral region. The system may further include multiple detectors in optical alignment with the optical subsystems. The detectors may be operative to receive the thermal infrared energy dispersed from the diffraction gratings within the MWIR spectral region and the LWIR spectral region and determine spectral component data associated with the thermal infrared energy in the MWIR spectral region and the LWIR spectral region. The system may further include a computing device having at least one processor. The computing device may be in communication with the detectors and operative to receive the spectral component data from the detectors and detect an atmospheric gas based on the spectral component data.

In some examples, the computing device may be operative to detect the atmospheric gas by comparing an atmospheric gas corresponding to the spectral component data in the MWIR spectral region to an atmospheric gas corresponding to the spectral component data in the LWIR spectral region to determine a match. In some examples, the detected atmospheric gas may be methane.

In some examples, the atmospheric gas may not be detected when the atmospheric gas corresponding to the spectral component data in the MWIR spectral region does not match the atmospheric gas corresponding to the spectral component data in the LWIR spectral region (e.g., a false positive).

In some examples, the computing device may be further operative to receive positioning data corresponding to a location of the detected atmospheric gas from a positioning device and update a spatial map with the positioning data and a concentration of the detected atmospheric gas. The spatial map may include multiple locations and concentrations of previously detected atmospheric gases.

In some examples, the optical subsystems may include multiple mirrors and the mirrors and the focusing elements may form multiple optical paths. In some examples, the optical subsystems may include a MWIR optical subsystem and a LWIR optical subsystem. In some examples, the MWIR optical subsystem may be co-aligned with the LWIR optical subsystem.

In one embodiment, a method utilized by the above-described system may include (1) receiving, at a collector, thermal infrared energy from a column of atmosphere, (2) receiving, at optical subsystems, the incoming thermal infrared energy at the collector over optical paths, (3) focusing the thermal infrared energy onto diffraction gratings that disperse the thermal infrared energy at a wavelength within a mid-wavelength infrared (MWIR) spectral region and a wavelength within a long-wavelength infrared (LWIR) spectral region, (4) receiving, at detectors, the thermal infrared energy dispersed from the diffraction gratings within the MWIR spectral region and the LWIR spectral region, (5) determining spectral component data associated with the thermal infrared energy in the MWIR spectral region and the LWIR spectral region, (6) sending the spectral component data to a computing device, and (7) identifying an atmospheric gas based on the spectral component data.

In some examples, portions of the above-described method may be encoded as computer-readable instructions on a non-transitory computer-readable medium. For example, a computer-readable medium may include one or more computer-executable instructions that, when executed by at least one processor of a computing device, may cause the computing device to (1) receive, from multiple detectors, spectral component data that is associated with thermal infrared energy at a wavelength within a mid-wavelength infrared (MWIR) spectral region and spectral component data that is associated with a wavelength within a long-wavelength infrared (LWIR) spectral region and (2) detect an atmospheric gas based on the spectral component data by (a) comparing a first atmospheric gas associated with the spectral component data in the MWIR spectral region to a second atmospheric gas corresponding to the spectral component data in the LWIR spectral region and (b) determining the atmospheric gas based on the comparison. Features from any of the above-mentioned embodiments may be used in combination with one another in accordance with the general principles described herein. These and other embodiments, features, and advantages will be more fully understood upon reading the following detailed description in conjunction with the accompanying drawings and claims.

DETAILED DESCRIPTION OF EXAMPLE EMBODIMENTS

Various embodiments are directed to the remote detection of greenhouse atmospheric gas. A collector may receive thermal infrared energy from a column of atmosphere. A first optical subsystem and a second optical subsystem may receive the thermal infrared energy at the collector over optical paths and focus the thermal infrared energy onto diffraction gratings. A first diffraction grating may disperse the thermal infrared energy within a mid-wavelength infrared (MWIR) band and a second diffraction grating may disperse the thermal infrared energy within a long-wavelength infrared (LWIR) band. Detectors may then receive the thermal infrared energy dispersed MWIR and LWIR bands and determine spectral component data corresponding to a concentration of an atmospheric gas. The detectors may send the spectral component data to a processor for identification of the atmospheric gas.

In accordance with the embodiments of the disclosure described herein, the accuracy of detecting greenhouse atmospheric gases, such as methane, is increased as compared to traditional methods. Various embodiments, as described herein, provide for the co-acquisition of both LWIR and MWIR hyperspectral imagery. The utilization of both LWIR and MWIR spectral methods for detecting atmospheric gases provides a robust and flexible set of tools for accurate detection under any atmospheric conditions, surface type, or scene heterogeneity (e.g., from urban to forested landscapes).

Embodiments of the disclosure now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
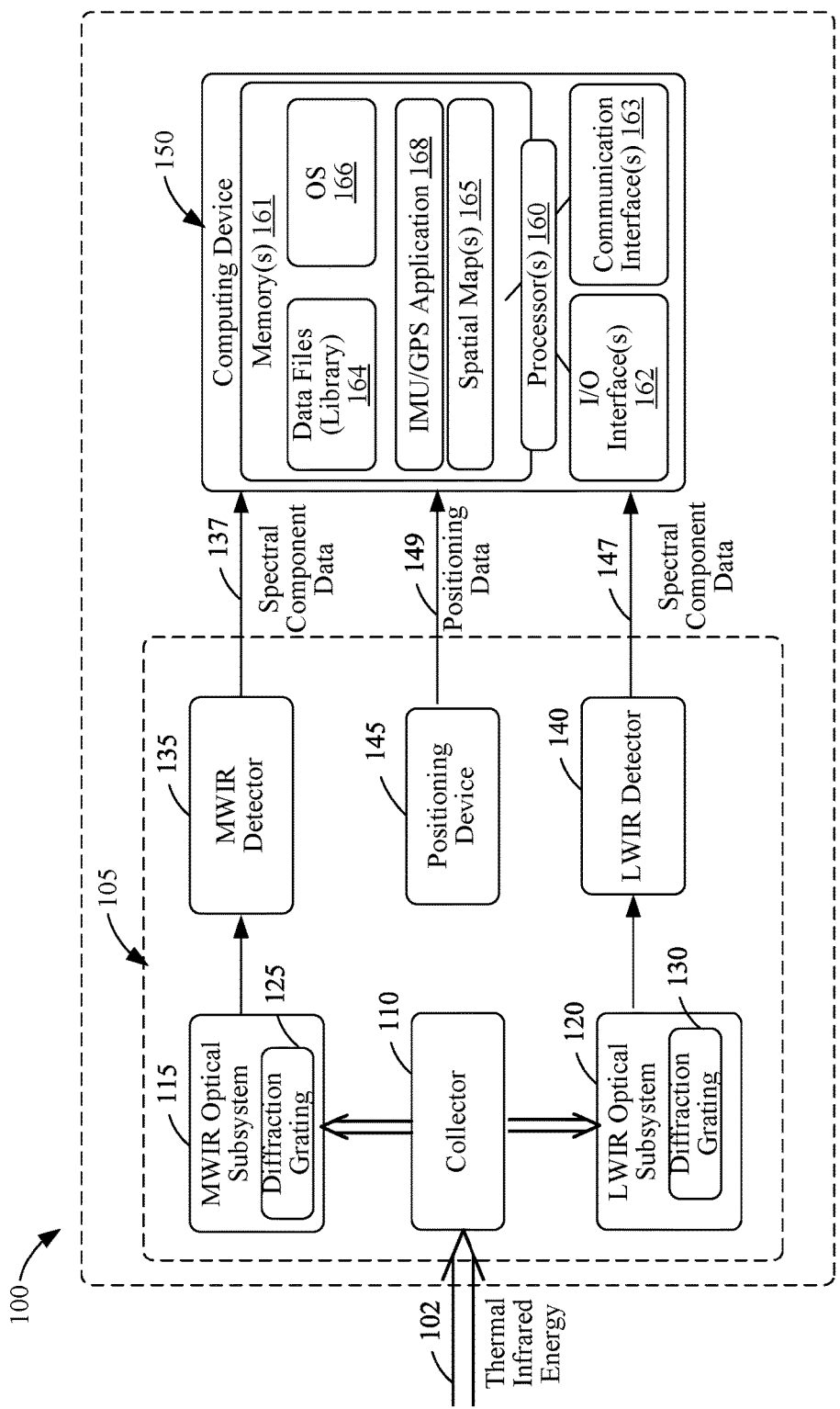
FIG. 1 illustrates a block diagram of an example system that may be utilized in accordance with various embodiments.

FIG. 1 represents a block diagram of an example system 100 for the remote detection of an atmospheric gas, according to various embodiments. The term "atmospheric gas," as used herein, generally refers to any atmospheric gas that absorbs and emits radiation within the thermal infrared range (e.g., a greenhouse gas). One example of a greenhouse gas is methane.

In one embodiment, the system 100 may be configured to be mounted to a mobile airborne platform (e.g., a UAV or manned aircraft) (not shown), capable of being flown at low above ground levels, for locating and quantifying methane gas leaks emanating from natural sources or infrastructure used in the oil and gas industry. In another embodiment, the system 100 may be configured to be mounted to a mobile ground-based platform (e.g., a motor vehicle) for locating and detecting methane from a ground level stand-off position. In yet another embodiment, the system 100 may be configured to be utilized as a handheld surface imager for locating and detecting methane from a surface.

As shown in FIG. 1, the system 100 may include a thermal infrared energy collection and detection device 105 which may include a collector 110, a MWIR optical subsystem 115, a LWIR optical subsystem 120, a MWIR detector 135, a LWIR detector 140, and a positioning system 145. The device 105 may be functionally coupled to a computing device 150.

In one embodiment, the collector 110 is an optical pathway configured to receive thermal infrared energy 102 radiating from a natural or constructed surface (e.g., the ground) and an overlying atmospheric column. The collector 110 may further be configured to redirect the thermal infrared energy 102 to both the MWIR optical subsystem 115 and the LWIR optical subsystem 120 which, in one embodiment, may include co-aligned or independent optical systems.

Each of the MWIR optical subsystem 115 and the LWIR optical subsystem 120 may incorporate one or more mirrors and a focusing element to form optical paths in order to achieve both a wide (e.g., 30 degree) field of view, optimal spectral dispersion, and a small form factor. For example, in some embodiments, each of the optical subsystems 115 and 120 may incorporate three or more mirrors and a focusing element for each optical path to achieve the aforementioned field of view while retaining a small form factor. In one embodiment, the collector 110 and subsystems 115 and 120 may include curved reflective optical mirrors which reflect and focus incoming light (i.e., the thermal infrared energy 102) onto dispersive diffraction gratings (e.g., diffraction gratings 125 and 130). The diffraction gratings 125 and 130 may each disperse light at different lines per millimeter and at different wavelengths. For example, the diffraction grating 125 may disperse light at 150 lines per millimeter with a blaze wavelength of 3.3 microns while the diffraction grating 130 may disperse light at 25 lines per millimeter with a blaze wavelength of 8 microns. It should be understood by those skilled in the art, that the diffraction gratings 125 and 130 may be blazed gratings (also known as echelette gratings) which is a form of reflective or transmission diffraction grating designed to produce the maximum grating efficiency in a specific diffraction order. Due to this design, a blazed grating operates at a specific wavelength, known as the blaze wavelength.

In one embodiment, the thermal infrared energy 102 (i.e., refractive light) from the diffraction grating 125 may be focused on a MWIR-sensitive insidium antimonide (InSb) focal plane array (e.g., the MWIR detector 135) and the thermal infrared energy 102 from the diffraction grating 130 may be focused on a LWIR-sensitive vanadium oxide microbolometer array (e.g., the LWIR detector 140). It should be understood that other MWIR-sensitive and LWIR-sensitive arrays may also be utilized.

In one embodiment, the optical subsystems 115 and 120 may capture the radiant spectral response of the emitted thermal infrared energy 102. For example, the MWIR optical subsystem 115 may capture a radiant spectral response of emitted energy from 3 microns to 4 microns while the LWIR optical subsystem 120 may capture a radiant spectral response of emitted energy from 7.5 microns to 11 microns. It should understood that the 3 micron to 4 micron and 7.5 micron to 11 micron regions may cover the major rotational and vibrational absorption features of methane and other greenhouse gases as well as other common geologic surface materials, thereby effectively allowing for the unique identification and discrimination of the gas and surface spectral components in an instantaneous field of view.

In one embodiment, spectral features in both the MWIR and LWIR thermal infrared regions (e.g., the spectral component data 137 and 147) may be captured by using each of the MWIR and LWIR detectors 135 and 140 (e.g., focal plane arrays) as a line scan spectral image. Furthermore, the movement of the system 100 across an area of interest (e.g., a surface and the overlying atmospheric column) may build a spectral map one line at a time across an along-track direction on an array while a cross-track direction of the array may capture the spatial distribution of energy as a function of an angular field of view. A full spectrum representation of the emitted energy may be represented by a pixel in a raster data cube.

The spectral component data 137 and 147 may be recorded as information on the computing device 150 as one or more data files 164. Each spectrum (e.g., pixel) in the spectral component data 137 and 147 may be deconvolved by the computing device 150 using a library of gas species and common geologic materials which may be stored in the data files 164. The resulting data (which may also be stored in the data files 164) may include relative abundances of surface and gas species, including methane gas calculated using both MWIR and LWIR spectral regions. In one embodiment, the computing device 150 may be configured to reconstruct a spatial map 165 of the aforementioned data results using positioning data 149 received from a positioning device 145 in the system 100. In one embodiment, the positioning data 149 may be projected onto a map (e.g., spatial maps 165) to display the locations and concentrations of the gas and surface spectral components.

In one embodiment, the computing device 150 may also be configured to collect location and look angle information (e.g., the positioning data 149) from the positioning device 145 (which may include an inertial measurement unit (IMU) and/or a global positioning system (GPS)). In various embodiments, the positioning device 145 may either be incorporated into or attached to the system 100.

It should be appreciated that when flown on an airborne platform, the system 100 may be capable of measuring the contribution of methane and other greenhouse gases to the spectral radiation coming from a well-constrained field of view of the earth's surface and the atmosphere between the surface and the system 100. Moreover, the system 100 may be configured such that it consists of a sufficiently small size and weight capable of being flown on a manned aircraft, an unmanned aircraft, or used as a handheld or mounted surface imager.

The computing device 150 may include any number of processor-driven devices, including, but not limited to, a mobile computer (e.g., a mobile phone, smartphone, tablet computing device, etc.), a desktop computing device, a laptop computing device, wearable devices (e.g., smart watches, smart glasses, etc.), an application-specific circuit, a minicomputer, a microcontroller, combinations of one or more of the same, or any other suitable processor-driven devices. The computing device 150 may utilize one or more processors 160 to execute computer-readable instructions that facilitate the general operation of the computing device 150 and/or the detection/identification of atmospheric gases from received spectral component data.

In addition to having one or more processors 160, the computing device 150 may further include and/or be associated with one or more memory devices 161, input/output ("I/O") interface(s) 162, and/or communication and/or network interface(s) 163. The memory 161 may be any computer-readable medium, coupled to the processor(s) 160, such as random access memory ("RAM"), read-only memory ("ROM"), and/or a removable storage device. The memory 161 may store a wide variety of data files 164 and/or various program modules, such as an operating system ("OS") 166, an IMU/GPS application 168 and one or more spatial maps 165.

The data files 164 may include any suitable data that facilitates the operation of the computing device 150 and/or interaction of the computing device 150 with one or more other components of the system 100 (e.g., the MWIR detector 135, the LWIR detector 140, and the positioning system 145). For example, the data files 164 may include information associated with the spectral component data 137, the spectral component data 147, and the positioning data 149 received from the device 105 in the system 100.

The OS 166 may be a suitable module that facilitates the general operation of the computing device 150, as well as the execution of other program modules. For example, the OS 166 may be, but is not limited to, Microsoft Windows®, Apple OSX™, Unix, a mainframe computer operating system (e.g., IBM z/OS, MVS, OS/390, etc.), or a specially designed operating system. In one embodiment, the OS 166 may be a suitable mobile OS or a specially designed operating system. As desired, the computing device 150 may additionally include one or more communication modules that facilitate interaction with other computing devices and/or other communications functionality. For example, a suitable near field communication module, radio frequency module, Bluetooth module, or other suitable communication module may be included in computing device 150.

The one or more I/O interfaces 162 may facilitate communication between the computing device 150 and one or more input/output devices; for example, one or more user interface devices, such as a display, a keypad, a touch screen display, a microphone, a speaker, etc., that facilitate user interaction with the computing device 150. The one or more network and/or communication interfaces 163 may facilitate connection of the computing device 150 to one or more suitable networks (not shown). In this regard, the computing device 150 may receive and/or communicate information to other components of the system 100 (such as the device 105).

The system 100 shown in and described with respect to FIG. 1 is provided by way of example only. Numerous other operating environments, system architectures, and/or device configurations are possible. Other system embodiments can include fewer or greater numbers of components and may incorporate some or all of the functionality described with respect to the system components shown in FIG. 1. Accordingly, embodiments of the disclosure should not be construed as being limited to any particular operating environment, system architecture, or device configuration.

Figure 2:
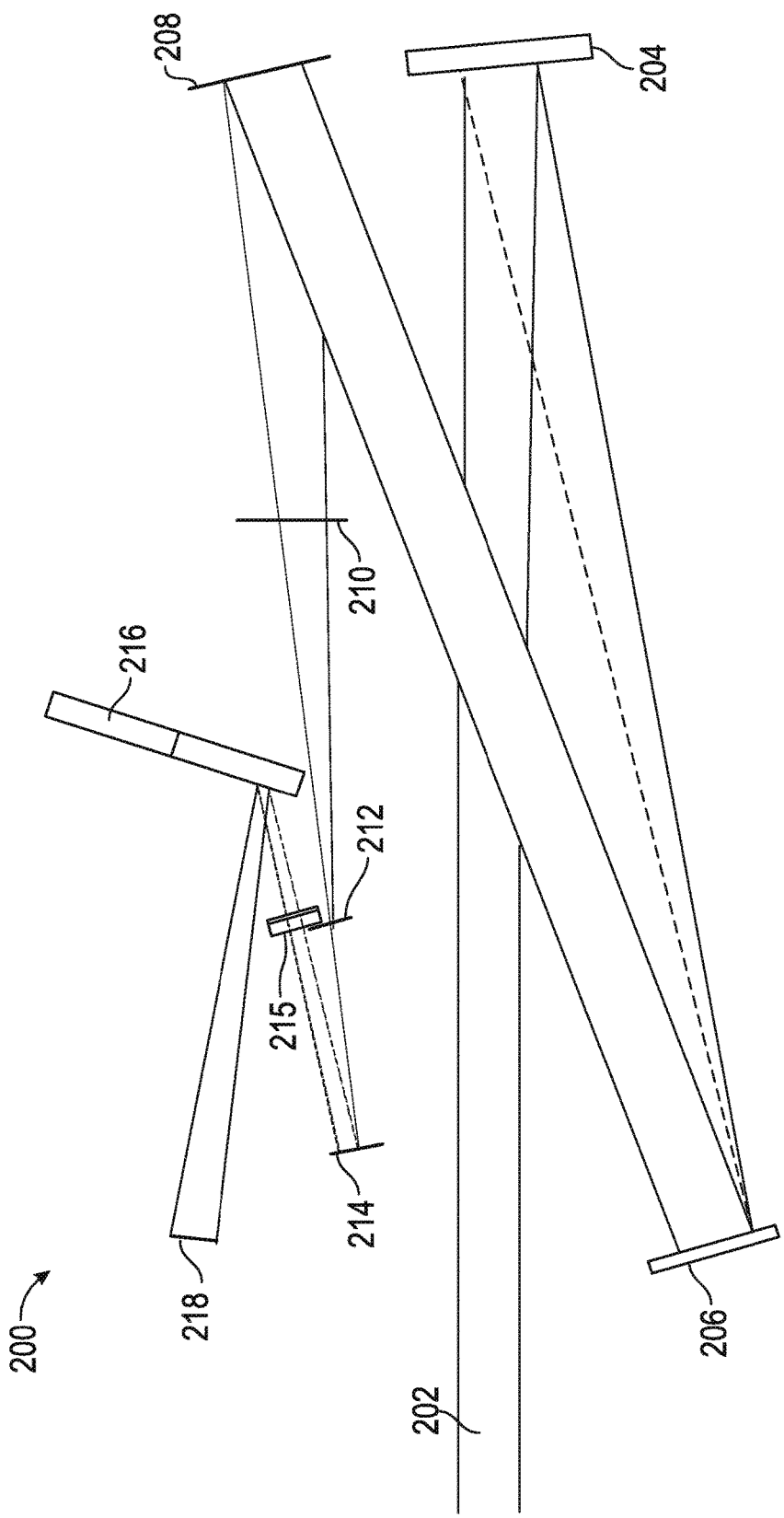
FIG. 2 illustrates a diagram of an optical model utilized by the example system of FIG. 1, according to an example embodiment.

FIG. 2 illustrates a diagram of an optical model 200 utilized by the example system of FIG. 1, according to an example embodiment.

Turning now to FIG. 2, the optical model 200 (which may correspond to the MWIR optical subsystem 115 or the LWIR optical subsystem 120) may include a number of elliptical and parabolic optical components or troughs (e.g., mirrors) used for focusing received thermal infrared energy 202 radiating from a ground surface and an overlying atmospheric column. For example, an elliptical trough 204 may focus the thermal infrared energy 202 to an elliptical trough 206 which in turn may focus the thermal infrared energy 202 to the parabolic trough 208. The parabolic trough 208 may then focus the thermal infrared energy 202 through an x-dimension slit 210 and a y-dimension slit 212 to an elliptical trough 214 which in turn may focus the thermal infrared energy 202 through a lens 215 onto a diffraction grating 216. The diffraction grating 216 may then disperse the thermal infrared energy 202 onto a detector 218 as described above with respect to FIG. 1.

In some embodiments, the elliptical and parabolic troughs 206 and 208 may be mirrors designed to have predetermined specifications to facilitate the focusing of the thermal infrared energy 202. For example, in an embodiment, four mirrors may be utilized having the following specifications: Mirror 1: Circular Trough, Radius of Curvature (ROC) X: 111.149 mm (acceptable range: 110 mm to 112 mm) ROC Y: Inf., Conic X: 0; Mirror 2: Elliptical Trough, ROC X: 152 mm (acceptable range: 150 mm to 154 mm) ROC Y: Inf., Conic X: −0.25 (range: −0.24 to −0.26) Full X Aperture: 60 mm Full Y; Mirror 3: Parabolic Trough, ROC X: Inf., ROC Y: 325 mm (acceptable range: 320 mm to 330 mm) Conic Y: −1 Full X; Mirror 4: Elliptical Trough, ROC X: Inf, ROC Y: 60 (acceptable range: 58 mm to 62 mm), Conic Y: −0.289 (range: −0.25 to −0.3). It is understood that the above descriptions are for purposes of illustration and are not meant to be limiting.

Figure 3:
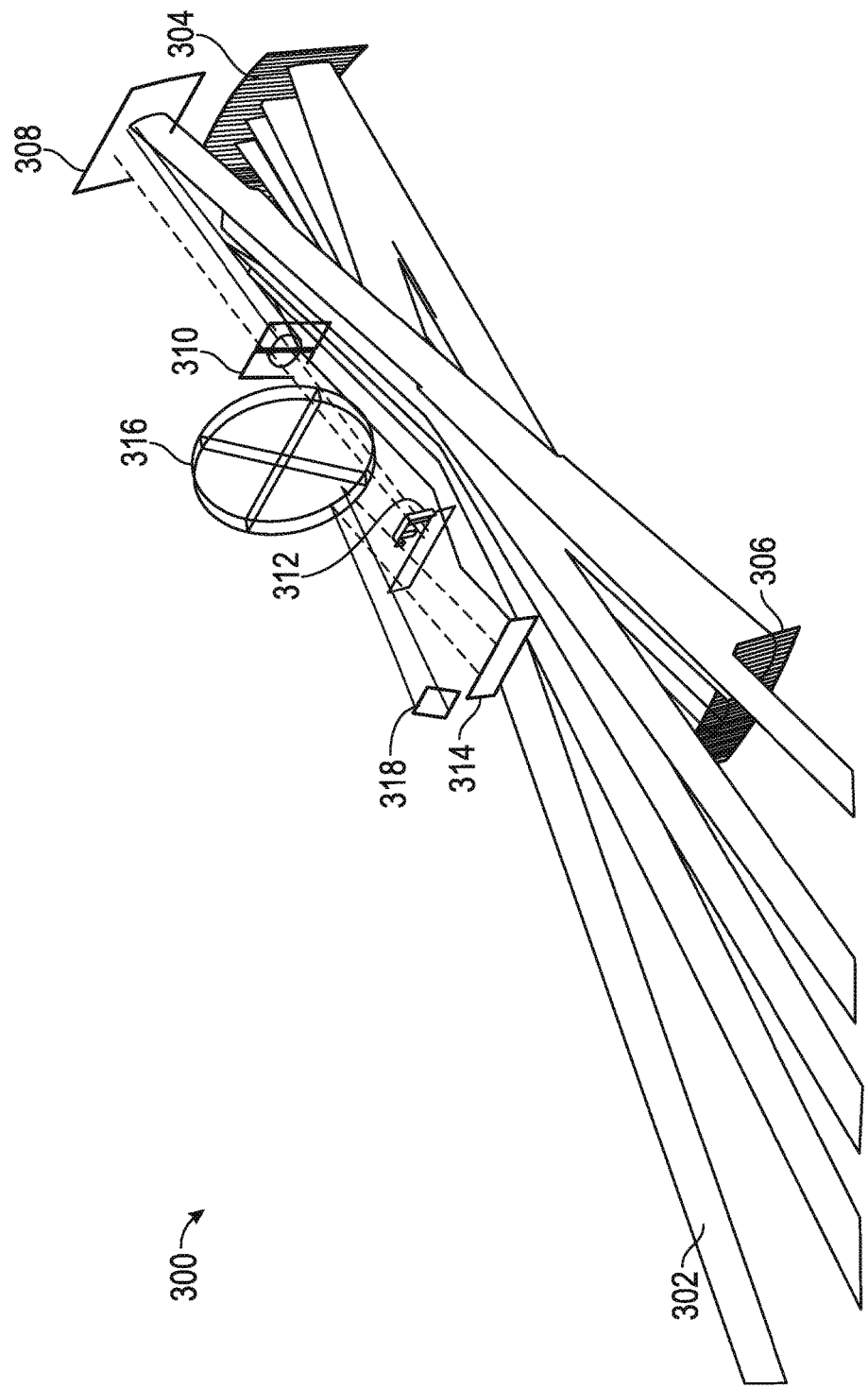
FIG. 3 illustrates a diagram of an optical model utilized by the example system of FIG. 1, according to another example embodiment.

FIG. 3 illustrates a diagram of a view of an optical model 300 utilized by the example system of FIG. 1, according to another example embodiment.

Turning now to FIG. 3, the optical model 300 which may correspond to the MWIR optical subsystem 115 or the LWIR optical subsystem 120. For example, if the optical model 200 (described above in FIG. 2) corresponds to the MWIR optical subsystem 115, then the optical model 300 may correspond to the LWIR optical subsystem 120. As another example, if the optical model 200 corresponds to the LWIR optical subsystem 120, then the optical model 300 may correspond to the MWIR optical subsystem 115.

In some embodiments, the optical model 300 may include a number of optical components or troughs (e.g., mirrors) used for focusing received thermal infrared energy 302 radiating from a ground surface and an overlying atmospheric column. For example, the trough 304 may focus the thermal infrared energy 302 to the trough 306 which in turn may focus the thermal infrared energy 302 to the parabolic trough 308. The parabolic trough 308 may then focus the thermal infrared energy 302 through slits 310 and 312 to a trough 314 which in turn may focus the thermal infrared energy 302 onto a diffraction grating 316. The diffraction grating 316 may then disperse the thermal infrared energy 302 onto a detector 318 as described above with respect to FIG. 1. In some embodiments, the elliptical and parabolic troughs 306 and 308 may be mirrors designed to have predetermined specifications to facilitate the focusing of the thermal infrared energy 302 similar to those as described above with respect to the elliptical and parabolic troughs 206 and 208 shown FIG. 2. It is understood that the above descriptions are for purposes of illustration and are not meant to be limiting.

Figure 4:
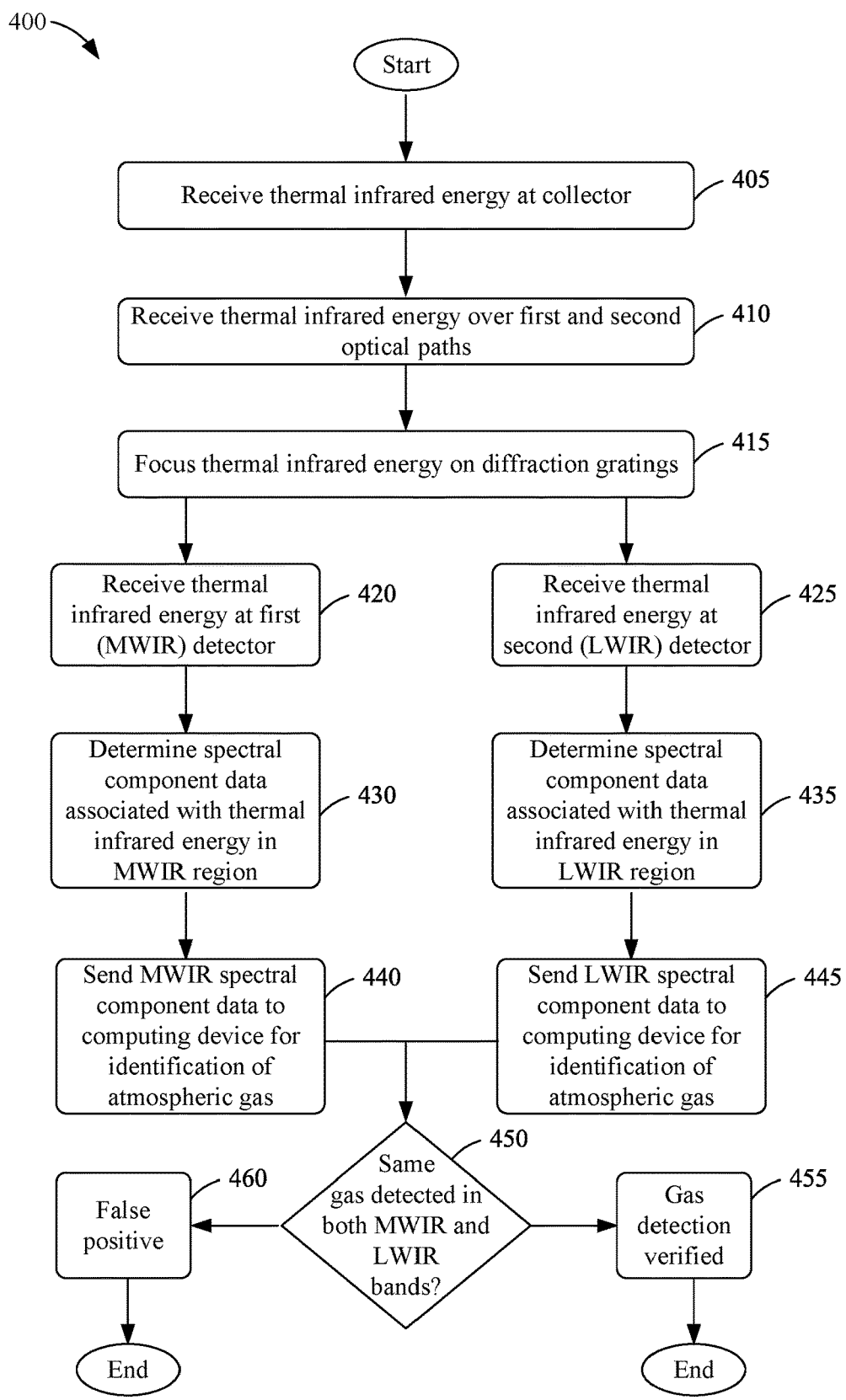
FIG. 4 illustrates a flow diagram of an example process for remotely detecting greenhouse atmospheric gas, according to an example embodiment.

FIG. 4 illustrates a flow diagram of an example process 400 for remotely detecting an atmospheric gas, according to an example embodiment. In certain embodiments, the operations of the example process 400 may be performed by the system 100 illustrated in FIG. 1. The method 400 may begin at block 405.

At block 405, the collector 110 may receive the thermal infrared energy 102 from a column of atmosphere. The collector 110 may receive the thermal infrared energy 102 in a variety of ways. For example, the collector 110 may be an optical pathway that receives the thermal infrared energy 102 as it is radiating from a natural or constructed surface (e.g., the ground) and an overlying atmospheric column.

At block 410, a first optical subsystem (e.g., the MWIR optical subsystem 115) and a second optical subsystem (e.g., the LWIR optical subsystem 120) may receive the thermal infrared energy 102 over first and second optical paths. The optical subsystems 115 and 120 may receive the thermal infrared energy 102 in a variety of ways. For example, the collector 110 may redirect the thermal energy 102 to both the MWIR optical subsystem 115 and the LWIR optical system 120. In one embodiment, the MWIR optical subsystem 115 and the LWIR optical system 120 may be co-aligned with one another. In another embodiment, the MWIR optical subsystem 115 and the LWIR optical system 120 may be independent optical subsystems.

At block 415, the first and second optical subsystems (e.g., the MWIR optical subsystem 115 and the LWIR optical subsystem 120) may focus the thermal infrared energy 102 onto a first diffraction grating (e.g., the diffraction grating 125) and a second diffraction grating (e.g., the diffraction grating 130).

The MWIR optical subsystem 115 and the LWIR optical subsystem 120 may focus the thermal infrared energy 102 onto the diffraction gratings 125 and 130 in a variety of ways. For example, in the MWIR optical subsystem 115, elliptical troughs 204, 206 and 214, parabolic trough 208, and lens 215 (shown in FIG. 2) may focus the thermal infrared energy 102 onto the diffraction grating 125. Similarly, in the LWIR optical subsystem 120, elliptical troughs 304, 306 and 314, parabolic trough 308, and lens 315 (shown in FIG. 3) may focus the thermal infrared energy 102 onto the diffraction grating 130. In one embodiment, the diffraction grating 125 may be configured to disperse the thermal infrared energy 102 at a first wavelength within a MWIR spectral region and the diffraction grating 130 may be configured to disperse the thermal infrared energy 102 at a second wavelength within a LWIR spectral region.

At block 420, a first detector (e.g., the MWIR detector 135) may receive the thermal infrared energy 102 dispersed from a first diffraction grating (e.g., the diffraction grating 125) within the MWIR spectral region.

At block 425, a second detector (e.g., the LWIR detector 140) may be configured to receive the thermal infrared energy 102 dispersed from a second diffraction grating (e.g., the diffraction grating 130) within the LWIR spectral region.

At block 430, the first detector may determine spectral component data associated with the thermal infrared energy 102 in the MWIR spectral region. For example, MWIR detector 135 may determine the spectral component data 137. In one embodiment, the spectral component data 137 may correspond to a concentration of one or more atmospheric gases. For example, the spectral component data 137 may correspond to a concentration of methane gas. The MWIR detector 135 may determine the spectral component data 137 in a variety of ways. For example, the spectral component data 137 may be determined from the radiant spectral response of the emitted thermal infrared energy 102 that correspond to major rotational and vibrational absorption features of methane and other greenhouse gases as well as other common geologic surface materials. For example, the MWIR detector 135 in the optical subsystem 115 may capture a radiant spectral response of emitted energy from 3 microns to 4 microns corresponding to concentration of methane and/or other greenhouse gases.

At block 435, the second detector may determine spectral component data associated with the thermal infrared energy 102 in the LWIR spectral region. For example, the LWIR detector 140 may determine the spectral component data 147. In one embodiment, the spectral component data 147 may correspond to a concentration of one or more atmospheric gases. For example, the spectral component data 147 may correspond to a concentration of methane gas. The LWIR detector 140 may determine the spectral component data 147 in a variety of ways. For example, the spectral component data 147 may be determined from the radiant spectral response of the emitted thermal infrared energy 102 that correspond to major rotational and vibrational absorption features of methane and other greenhouse gases as well as other common geologic surface materials. For example, the LWIR detector 140 in the optical subsystem 120 may capture a radiant spectral response of emitted energy from 7.5 microns to 11 microns corresponding to a concentration of methane and/or other greenhouse gases.

At block 440, the first detector may send the spectral component data to a computing device for identification of one or more atmospheric gases. For example, the MWIR detector 135 may be configured to send the spectral component data 137 to the computing device 150 for identification of one or more atmospheric gases in the MWIR region.

At block 445, the second detector may send the spectral component data to a computing device for identification of one or more atmospheric gases. For example, the LWIR detector 140 may be configured to send the spectral component data 147 to the computing device 150 for identification of one or more atmospheric gases in the LWIR region.

At block 450, the computing device may determine whether an atmospheric gas detected in the MWIR region by the first detector is in agreement with an atmospheric gas detected in the LWIR region by the second detector. For example, the computing device 150 may compare the spectral component data 137 received from the MWIR detector 135 in the MWIR band to the spectral component data 147 received from the LWIR detector 140 to determine if the same atmospheric gas is detected in the LWIR band. If the computing device 150 determines that an atmospheric gas corresponding to the spectral component data 137 matches an atmospheric gas corresponding to the spectral component data 147, then the process 400 continues to block 455 where the computing device 150 may verify that a particular atmospheric gas (e.g., methane) has been detected. If the computing device 150 determines that an atmospheric gas corresponding to the spectral component data 137 does not match an atmospheric gas corresponding to the spectral component data 147, then the process 400 continues to block 460 where the computing device 150 may identify and indicate a false positive with respect to the detection of a particular atmospheric gas.

Various embodiments of the invention are described above with reference to block and flow diagrams of systems, methods, apparatuses, and/or computer program products according to example embodiments. It will be understood that one or more blocks of the block diagrams and flow diagrams, and combinations of blocks in the block diagrams and the flow diagrams, respectively, can be implemented by computer-executable program instructions. Likewise, some blocks of the block diagrams and flow diagrams may not necessarily need to be performed in the order presented, or may not necessarily need to be performed at all, according to some embodiments.

Various block and/or flow diagrams of systems, methods, apparatus, and/or computer program products according to example embodiments are described above. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments.

The computer-executable program instructions may be loaded onto a special purpose computer or other particular machine, a processor, or other programmable data processing apparatus to produce a particular machine, such that the instructions that execute on the computer, processor, or other programmable data processing apparatus create means for implementing one or more functions specified in the flow diagram block or blocks. The computer program instructions may also be stored in a non-transitory computer-readable memory that can direct a computer or other programmable data processing apparatus to function in a particular manner, such that the instructions stored in the non-transitory computer-readable memory produce an article of manufacture including instruction means that implement one or more functions specified in the flow diagram block or blocks. As an example, embodiments of the may provide for a computer program product, comprising a computer-usable medium having a computer-readable program code or program instructions embodied therein, said computer-readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of means for performing the specified functions, combinations of elements or steps for performing the specified functions and program instruction means for performing the specified functions. It will also be understood that each block of the block diagrams and flow diagrams, and combinations of blocks in the block diagrams and flow diagrams, can be implemented by special purpose, hardware-based computer systems that perform the specified functions, elements or steps, or combinations of special purpose hardware and computer instructions.

Many modifications and other embodiments of the invention set forth herein will be apparent having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A system comprising:
a collector that receives thermal infrared energy from at least one atmospheric column;
a plurality of optical subsystems comprising focusing elements and a plurality of diffraction gratings in optical alignment with the collector, wherein a first diffraction grating among the plurality of diffraction gratings disperses the thermal infrared energy at a predetermined number of lines per millimeter and a predetermined blaze wavelength, wherein a second diffraction grating among the plurality of diffraction gratings disperses the thermal infrared energy at a number of lines per millimeter below the predetermined number of lines per millimeter associated with the first diffraction grating and at a blaze wavelength above the predetermined blaze wavelength associated with the first diffraction grating, wherein the optical subsystems are operative to:
receive the thermal infrared energy; and
focus, with the focusing elements, the thermal infrared energy onto the diffraction gratings, wherein the diffraction gratings disperse the thermal infrared energy at a wavelength within a mid-wavelength infrared (MWIR) spectral region and a wavelength within a long-wavelength infrared (LWIR) spectral region;
a plurality of detectors in optical alignment with the optical subsystems, wherein the detectors are operative to:
receive the thermal infrared energy dispersed from the diffraction gratings within the MWIR spectral region and the LWIR spectral region; and
determine spectral component data associated with the thermal infrared energy in the MWIR spectral region and the LWIR spectral region; and
a computing device comprising at least one processor, wherein the computing device is in communication with the detectors and is operative to:
receive the spectral component data from the detectors; and
detect a target atmospheric gas based on the spectral component data, wherein the computing device is operative to detect the target atmospheric gas based on the spectral component data by comparing a first atmospheric gas corresponding to the spectral component data in the MWIR spectral region to a second atmospheric gas corresponding to the spectral component data in the LWIR spectral region, wherein the target atmospheric gas has been detected when the first atmospheric gas corresponding to the spectral component data in the MWIR spectral region matches the second atmospheric gas corresponding to the spectral component data in the LWIR spectral region, wherein the target atmospheric gas is a greenhouse gas, wherein the match is determined when the first atmospheric gas corresponds to rotational and vibrational absorption features associated with a concentration of the greenhouse gas and the second atmospheric gas corresponds to the rotational and vibrational absorption features associated with concentration of the greenhouse gas, wherein the match does not occur when at least one of the first atmospheric gas or the second atmospheric gas corresponds to a concentration of a non-greenhouse gas.

2. The system of claim 1, wherein the computing device is further operative to:
receive positioning data corresponding to a location of the detected target atmospheric gas from a positioning device; and
update a spatial map with the positioning data and a concentration of the detected target atmospheric gas, wherein the spatial map comprises a plurality of locations and concentrations of previously detected atmospheric gases.

3. The system of claim 1, wherein the optical subsystems further comprise at least three mirrors, wherein the mirrors and the focusing elements form a plurality of optical paths comprising at least a thirty-degree field of view.

4. The system of claim 1, wherein the optical subsystems comprise a MWIR optical subsystem and a LWIR optical subsystem.

5. The system of claim 4, wherein the MWIR optical subsystem is co-aligned with the LWIR optical subsystem.

6. The system of claim 1, wherein the greenhouse gas comprises methane gas.

7. A method for detecting an atmospheric gas comprising:
receiving, at a collector, thermal infrared energy from at least one atmospheric column;
receiving, at a plurality of optical subsystems, the thermal infrared energy over a plurality of optical paths, the optical subsystems comprising focusing elements and a plurality of diffraction gratings in optical alignment with the collector, wherein a first diffraction grating among the plurality of diffraction gratings disperses the thermal infrared energy at a predetermined number of lines per millimeter and a predetermined blaze wavelength, wherein a second diffraction grating among the plurality of diffraction gratings disperses the thermal infrared energy at a number of lines per millimeter below the predetermined number of lines per millimeter associated with the first diffraction grating and at a blaze wavelength above the predetermined blaze wavelength associated with the first diffraction grating;
focusing, with the focusing elements, the thermal infrared energy onto the diffraction gratings, wherein the diffraction gratings disperse the thermal infrared energy at a wavelength within a mid-wavelength infrared (MWIR) spectral region and a wavelength within a long-wavelength infrared (LWIR) spectral region;
receiving, at a plurality of detectors, the thermal infrared energy dispersed from the diffraction gratings within the MWIR spectral region and the LWIR spectral region;
determining, at the detectors, spectral component data associated with the thermal infrared energy in the MWIR spectral region and the LWIR spectral region;
sending, from the detectors, the spectral component data to a computing device comprising at least one processor; and
detecting, by the computing device, a target atmospheric gas based on the spectral component data, wherein the computing device is operative to detect the target atmospheric gas based on the spectral component data by comparing a first atmospheric gas corresponding to the spectral component data in the MWIR spectral region to a second atmospheric gas corresponding to the spectral component data in the LWIR spectral region, wherein the target atmospheric gas has been detected when the first atmospheric gas corresponding to the spectral component data in the MWIR spectral region matches the second atmospheric gas corresponding to the spectral component data in the LWIR spectral region, wherein the target atmospheric gas is a greenhouse gas, wherein the match is determined when the first atmospheric gas corresponds to rotational and vibrational absorption features associated with a concentration of the greenhouse gas and the second atmospheric gas corresponds to the rotational and vibrational absorption features associated with concentration of the greenhouse gas, wherein the match does not occur when at least one of the first atmospheric gas or the second atmospheric gas corresponds to a concentration of a non-greenhouse gas.

8. The method of claim 7, further comprising:
receiving positioning data corresponding to a location of the detected target atmospheric gas from a positioning device; and
updating a spatial map with the positioning data and a concentration of the detected target atmospheric gas, wherein the spatial map comprises a plurality of locations and concentrations of previously detected atmospheric gases.

9. The method of claim 7, wherein the optical subsystems comprise a MWIR optical subsystem and a LWIR optical subsystem.

10. The method of claim 9, wherein the MWIR optical subsystem is co-aligned with the LWIR optical subsystem.

11. The method of claim 7, wherein the greenhouse gas comprises methane gas.

12. A non-transitory computer-readable medium comprising one or more computer-readable instructions that, when executed by at least one processor of a computing device, cause the computing device to:
receive spectral component data from a plurality of detectors, wherein the spectral component data is associated with thermal infrared energy from at least one atmospheric column at a wavelength within a mid-wavelength infrared (MWIR) spectral region and a wavelength within a long-wavelength infrared (LWIR) spectral region, wherein the thermal infrared energy is received from a collector, at a plurality of optical subsystems, over a plurality of optical paths, the optical subsystems comprising focusing elements and a plurality of diffraction gratings in optical alignment with the collector, wherein a first diffraction grating among the plurality of diffraction gratings disperses the thermal infrared energy at a predetermined number of lines per millimeter and a predetermined blaze wavelength, wherein a second diffraction grating among the plurality of diffraction gratings disperses the thermal infrared energy at a number of lines per millimeter below the predetermined number of lines per millimeter associated with the first diffraction grating and at a blaze wavelength above the predetermined blaze wavelength associated with the first diffraction grating; and
detect an atmospheric gas based on the spectral component data, wherein the atmospheric gas is detected by:
comparing a first atmospheric gas associated with the spectral component data in the MWIR spectral region to a second atmospheric gas corresponding to the spectral component data in the LWIR spectral region; and
determining a target atmospheric gas based on the comparison, wherein the computing device is operative to detect the target atmospheric gas based on the spectral component data by comparing a first atmospheric gas corresponding to the spectral component data in the MWIR spectral region to a second atmospheric gas corresponding to the spectral component data in the LWIR spectral region, wherein the target atmospheric gas has been detected when the first atmospheric gas corresponding to the spectral component data in the MWIR spectral region matches the second atmospheric gas corresponding to the spectral component data in the LWIR spectral region, wherein the target atmospheric gas is a greenhouse gas, wherein the match is determined when the first atmospheric gas corresponds to rotational and vibrational absorption features associated with a concentration of the greenhouse gas and the second atmospheric gas corresponds to the rotational and vibrational absorption features associated with concentration of the greenhouse gas, wherein the match does not occur when at least one of the first atmospheric gas or the second atmospheric gas corresponds to a concentration of a non-greenhouse gas.

13. The non-transitory computer-readable medium of claim 12, wherein the greenhouse gas comprises methane gas.

* * * * *